United States Patent [19]

Heller et al.

[11] Patent Number: 4,957,998
[45] Date of Patent: Sep. 18, 1990

[54] POLYMERS CONTAINING ACETAL, CARBOXY-ACETAL, ORTHO ESTER AND CARBOXYORTHO ESTER LINKAGES

[75] Inventors: Jorge Heller, Woodside; Steve Y. W. Ng, San Francisco; Donald W. H. Penhale, Menlo Park, all of Calif.

[73] Assignee: Pharmaceutical Delivery Systems, Inc., Menlo Park, Calif.

[21] Appl. No.: 234,806

[22] Filed: Aug. 22, 1988

[51] Int. Cl.$^5$ .................. C08G 63/06; C08G 67/00
[52] U.S. Cl. ................... 528/220; 528/361; 528/392; 525/43; 525/186
[58] Field of Search .......... 528/220, 361, 392; 525/43, 186

[56] References Cited

U.S. PATENT DOCUMENTS

| | | | |
|---|---|---|---|
| 2,957,856 | 10/1960 | Guest et al. | 528/392 |
| 4,093,709 | 6/1978 | Choi et al. | 424/19 |
| 4,131,648 | 12/1978 | Choi et al. | 424/22 |
| 4,139,344 | 2/1979 | von der Eltz | 8/21 |
| 4,180,646 | 12/1979 | Choi et al. | 528/392 |
| 4,304,767 | 12/1981 | Heller et al. | 424/78 |
| 4,549,010 | 10/1985 | Sparer et al. | 528/392 |
| 4,707,540 | 11/1987 | Manser et al. | 528/361 |

Primary Examiner—Kriellion Morgan
Attorney, Agent, or Firm—Dianne E. Reed

[57] ABSTRACT

Biodegradable polymers that are useful for making biodegradable sustained release agent dispensers and which contain acetal, carboxy-acetal, ortho ester and/or carboxy-ortho ester linkages.

39 Claims, 1 Drawing Sheet

POLYMERS CONTAINING ACETAL, CARBOXY-ACETAL, ORTHO ESTER AND CARBOXYORTHO ESTER LINKAGES

TECHNICAL FIELD

The invention is in the field of polymers containing hydrolytically labile linkages and relates generally to novel polymers having acetal, carboxy-acetal, ortho ester and carboxy-ortho ester linkages. The invention also relates to bioerodible or biodegradable devices fabricated from the novel polymers, which devices are useful for dispensing beneficial agents.

BACKGROUND ART

Interest in synthetic biodegradable polymers for the systemic delivery of therapeutic agents began in the early 1970's with the work of Yolles et al. on poly(lactic acid). Since that time numerous other polymers have been made and investigated for such use.

U.S. Pat. Nos. 4,093,709; 4,131,648; 4,139,344; and 4,180,646 describe biodegradable or bioerodible poly-(ortho ester) polymers These polymers result from reaction of an ortho ester (or ortho carbonate) such as 2,2-diethoxytetrahydrofuran, with a diol such as 1,4-cyclohexanedicarbinol. The reaction must be carried out at elevated temperature under reduced pressure and requires a relatively long reaction time. Drug or other active agent is dispersed in the polymer and is released therefrom as the polymer biodegrades due to hydrolysis of the labile linkages U.S. Pat. No. 4,304,767 describes another type of poly(ortho ester) which is made by reacting a polyol with a polyfunctional ketene acetal. The polymers of the present invention are also prepared using a polyfunctional ketene acetal as the starting material, but the present method is based on a two-step process whereby the polyfunctional ketene acetal is first reacted with varying molar ratios of a compound containing a vinyl ether, and the intermediate so prepared is then converted to a polymer by reaction with a polyol or polyacid. Using this procedure, polymers containing acetal, carboxy-acetal, ortho ester and carboxy-ortho ester linkages can be prepared.

Introduction of acetal, carboxy-acetal, ortho ester and carboxy-ortho ester groups between the various mer units as enabled by the presently disclosed process provides a means for controlling the rate at which the polymer biodegrades. Specifically, we have found that the rate of hydrolysis of polymers containing only acetal linkages is relatively slow while the rate of hydrolysis of polymers containing only carboxy-ortho ester linkages is very fast, with rates of hydrolysis of polymers containing only ortho ester or only carboxy-acetal linkages occupying intermediate values. Thus, by controlling the relative amounts of these four types of linkages between the various mer units, one can control the rate at which the polymer as a whole biodegrades.

DISCLOSURE OF THE INVENTION

The present invention provides novel biodegradable polymers, a process for making those polymers, and biodegradable devices fabricated from the novel biodegradable compounds which are useful for delivering beneficial agents.

The process for making these polymers comprises (i) reacting a diketene acetal of formula (I) where X is a quadrivalent organic group and A and B are hydrogen or lower alkyl, with a mono-hydroxy vinyl ether or monocarboxy vinyl ether of formulae (II) and (III), respectively, where $R^1$ and $R^2$ may be the same or different and are hydrocarbyl, oxyhydrocarbyl or aryl, and (ii) reacting the product of step (i) with a diol, a diacid or a hydroxy acid.

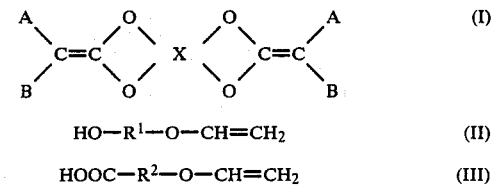

In step (i), reaction of compound (I) with either one to two moles of compounds (II) and/or (III) leads to the formation of the following intermediate monomers:

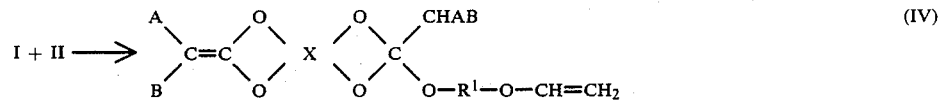

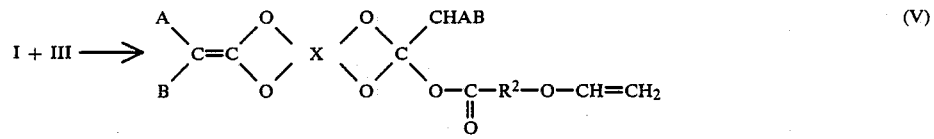

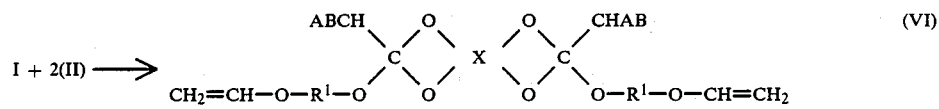

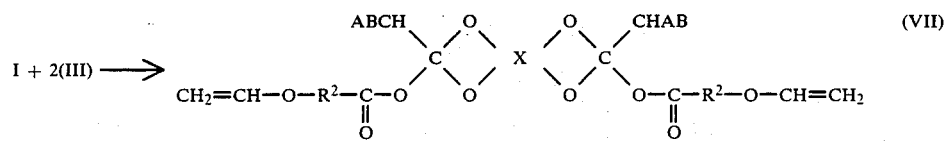

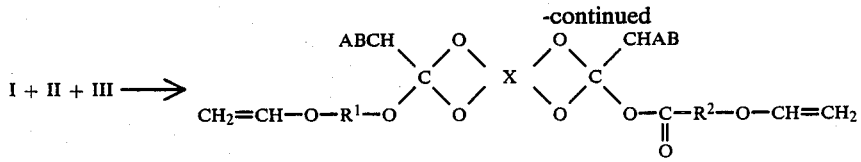

In step (ii), polymers are obtained by the reaction of the intermediates prepared in step (i) with compounds having the following general structure: $R'(OH)_n$ (IX); $R''(COOH)_n$ (X); or $R'''(OH)_l(COOH)_m$ (XI), where R', R" and R'" are as defined for $R^1$ and $R^2$, 1 n is an integer equal to 2 or more, and l and m are integers equal to 1 or more and may be the same or different. Typically, these latter reactants have 2 or 3 functionalities, (n or [l+m] is 2 or 3), but the compounds may be polyfunctional as well, e.g., they may be relatively high molecular weight polyols and/or polycarboxylic acids.

When these compounds are bifunctional, i.e., n=2 for compounds (IX) or (X) or l=1 and m=1 for compound (XI), linear polymers are obtained. When n=3 ore or when the sum of l and m is equal to 3 or more, crosslinked, rather than linear, polymers are obtained.

The biodegradable polymers of the invention, i.e, as prepared in the aforementioned step, are characterized by containing at least one of the following mer units:

Carboxy-Acetal/Carboxy-Ortho Ester

Polymers having combinations of any of the foregoing linkages may be obtained by varying the choice and quantity of reagents used.

The bioerodible devices of the invention comprise bodies of the biodegradable polymer admixed with a beneficial agent or coated into a beneficial agent composition.

MODES FOR CARRYING OUT THE INVENTION

Figure 1:
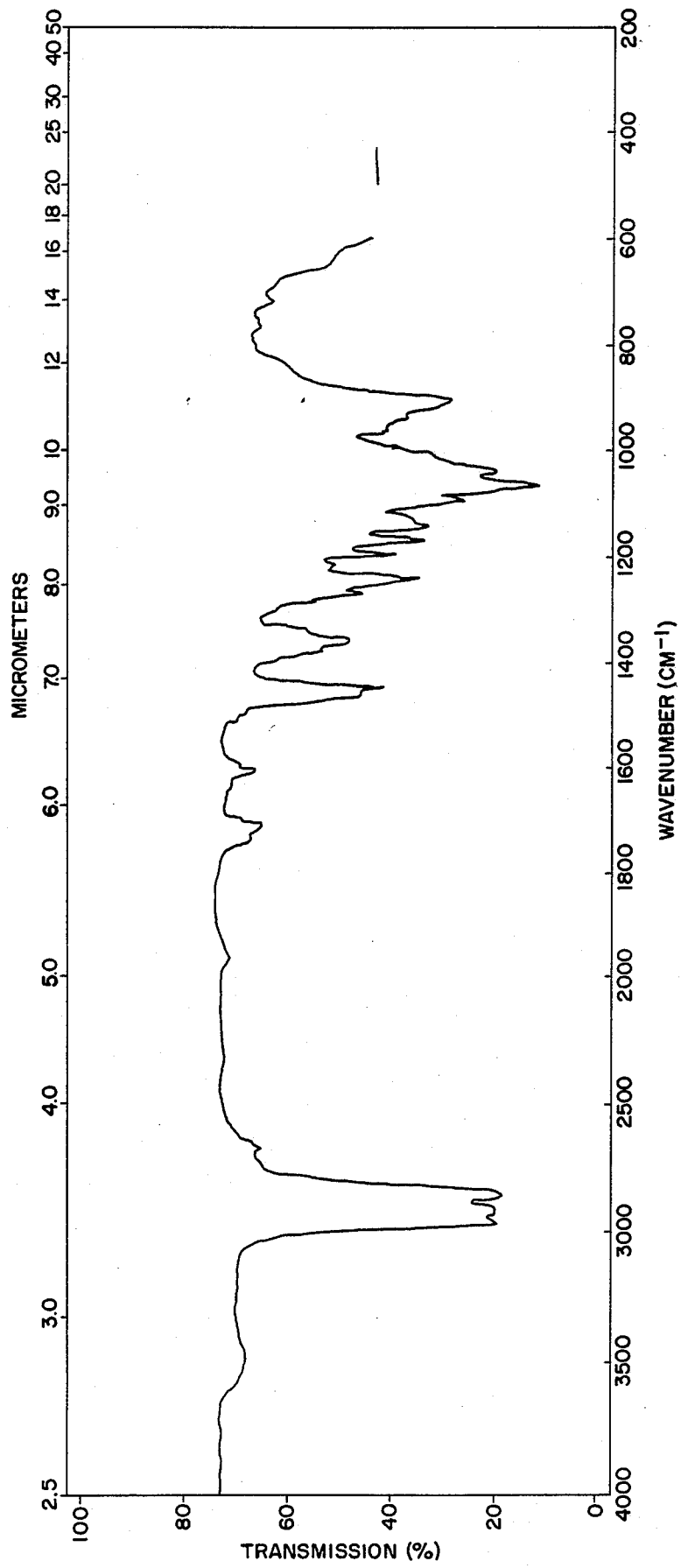
FIG. 1 is an infrared spectrum of the polymer obtained in Example 1.

The term "mer" intends the structurally recurring units or monomer units of the polymers of the invention. The mers of a given polymer may be the same or different, and when different, may be arranged in block or random fashion. When the mers of a polymer are the same, the polymer is called a homopolymer; when they are different, the polymer is called a copolymer.

The term "biodegradable", as used herein to describe the invention polymers, is synonymous with the art term "bioerodible" and intends a solid, gel, or viscous polymer that completely solubilizes as a consequence of hydrolysis.

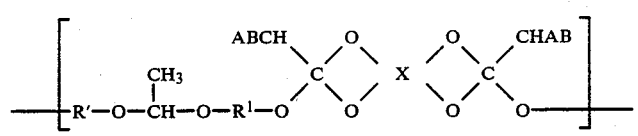

Acetal/Ortho Ester

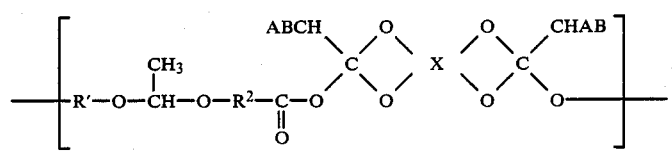

Acetal/Carboxy-Ortho Ester

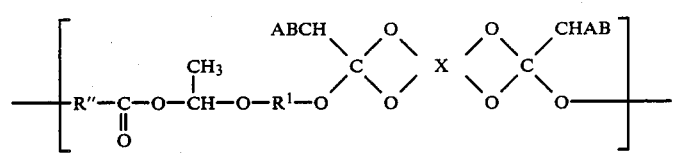

Carboxy-Acetal/Ortho Ester

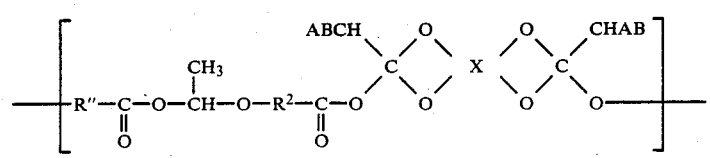

The term "beneficial agent" as used herein intends a compound or composition of matter that provides a desired and useful effect upon the environment or individual (man or animal) to which it is administered. This term includes, without limitation, agents such as drugs, nutrients, plant growth regulants, pesticides, catalysts, disinfectants, and the like.

The term "drug" as used herein intends a compound or composition of matter which when administered to an individual (man or animal) induces a desired pharmacologic and/or physiologic effect by local and/or systemic action. In general, the term includes the therapeutic or prophylactic agents in all major therapeutic/prophylactic areas of medicine.

The term "effective amount" as used herein intends that quantity of agent that is required to provide the desired or intended beneficial effect without intolerable side effects, such as toxicity.

"Lower alkyl" is intended to mean linear or branched alkyl moieties having 1 to 10, more typically 1 to 6 carbon atoms.

The X grouping in the above formulae is a quadrivalent organic moiety which may be, for example, $$-H_2C\diagdown\phantom{C}\diagup CH_2- \atop \phantom{-H_2}C \atop -H_2C\diagup\phantom{C}\diagdown CH_2-$$ (XVI)

a tetra-substituted cyclohexyl ring, or the like. A and B, as noted, are hydrogen or lower alkyl and may be the same or different. Examples of suitable diketene acetal monomer are given in Table I.

TABLE I

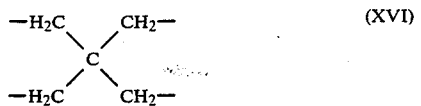

Compound I

Compound II

Compound III

Compound IV

Compound V

Compound VI

The symbols $R^1$, $R^2$, $R'$, $R''$ and $R'''$ in the formulae may be the same or different, and typically represent a hydrocarbyl or oxyhydrocarbyl group of 1 to 14 carbon atoms, usually 2 to 9 carbon atoms. The number of oxy (—O—) groups in the oxyhydrocarbyl molecule will typically be 1 to 4. The hydrocarbyl group will preferably be saturated, branched- or straight-chain aliphatic or saturated cycloaliphatic, unsubstituted or substituted with one or more moieties which will not interfere with the polymerization reaction, e.g., lower alkyl, amino, nitro, halogen, or the like.

The R moieties may also be aryl, in which case they are preferably carbocyclic, and may be monocyclic or polycyclic (fused) of 2 to 4 rings, but usually have 6 to 12 carbon atoms. Examples of such groups are unsubstituted or substituted with one or more substituents, e.g., lower alkyl, amino, nitro, halogen, and the like.

The number of repeating mer units in the polymer will normally be in the range of 2 to 1000, preferably 2 to 200, and most preferably 5 to 200.

The reactant introduced in step (ii), i.e., one given by formula (IX), (X) or (XI), is preferably a compound in which the hydroxy groups or carboxy groups are bound to aliphatic chains, present as substituents on six-membered carbocyclic or aromatic rings, or are terminal in linear polyesters or polyethers. Examples of such compounds are the following: tetraethylene glycol, bisphenol A, $HO_2C(CH_2)_4CO_2H$, $HO(CH_2)_5CO_2H$,

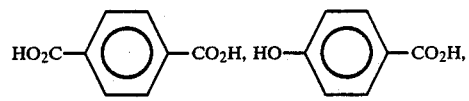

and the like.

In some cases, or example where crosslinked product is preferred, it may be desirable to use compounds which contain more than two reactive groups, e.g., polyethylene glycol, hydroxy-terminated polycaprolactone, etc.

The polymers are made via: (i) a condensation reaction between the selected diketene acetal and the hydroxyl and/or carboxyl-containing co-reactant, in the presence of a suitable catalyst; and (ii) subsequent reaction of the product with a compound having two or more reactive groups. The process is thus carried out as a two-step reaction.

The process may be carried out neat (no solvent) or in aprotic solvents such as tetraethylhydrofuran (THF), glyme (ethylene glycol dimethyl ether), diglyme, cymene, cumene, and chlorinated hydrocarbons. In either case, care should be taken to maintain anhydrous conditions. The reaction of step (i) will normally be run at room temperature, while the reaction of step (ii) will normally be run at temperatures in the range of 20° to 150° C., preferably 20° to 75 °C. The intermediate, i.e., the reaction product of step (i), may or may not be isolated prior to initiating the step (ii) reaction. The approximate mol ratio of reactants in step (i) is typically about 1:1 but can be varied depending on the product desired. The preferred approximate mol ratio in step (ii) (reaction product of step (i):diol) is typically about 1:1, but can be varied as well. While these ratios may be altered slightly, significant variation is not desirable as the molecular weight range of the product is dependent on the mol ratios of the reactants. The exact range of each reactant which will provide the desired product is dependent upon the purity and volatility of the reactant.

It may be desirable in some instances to carry out steps (i) or (ii) catalytically. Where the reactants are acidic, a catalyst is typically unnecessary. In the event that none of the reactants are acidic (e.g., in the reactions shown in Schemes 1 and 3 below), an acid catalyst should be used. Examples of suitable acid catalysts include p-toluenesulfonic acid, methanesulfonic acid. Where a catalyst is used, it is preferred that the catalytic compound be immobilized on a suitable solid support.

The following schemes illustrate the various synthetic routes embraced by the present invention. They are presented for purposes of illustration only and do not represent a complete listing of all possible reaction schemes.

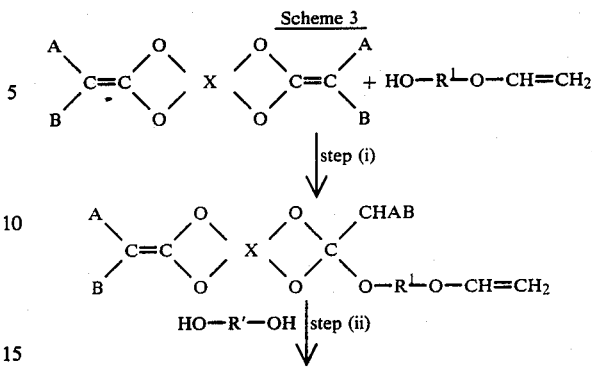

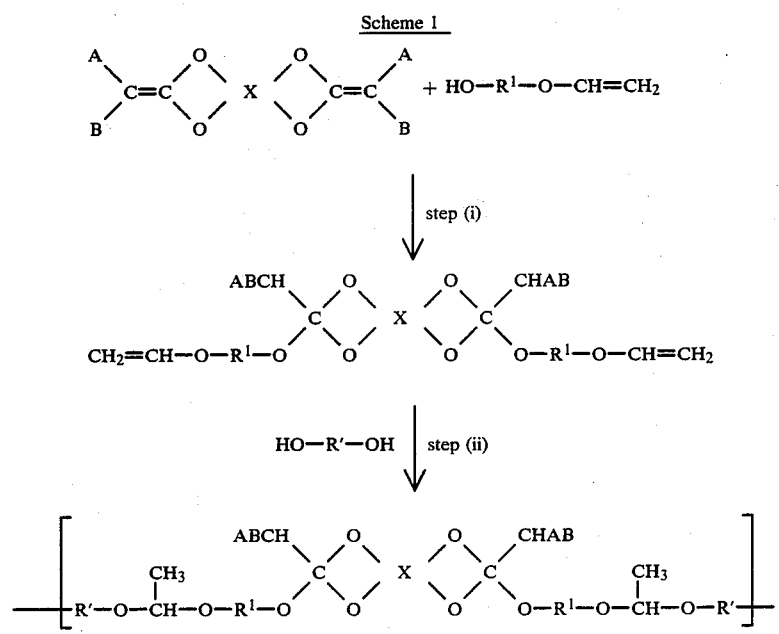

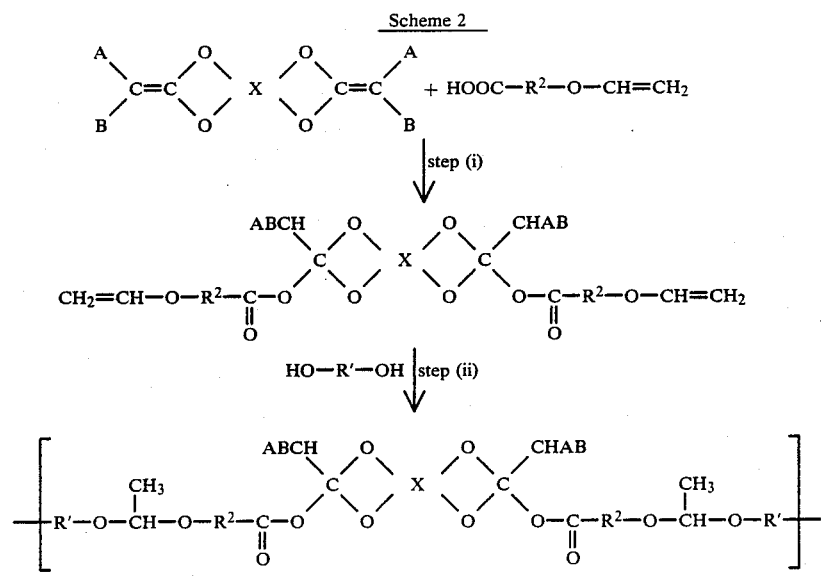

-continued
Scheme 3

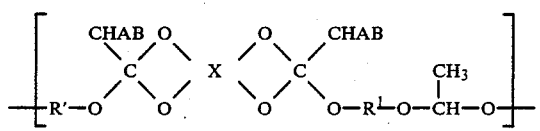

Scheme 4

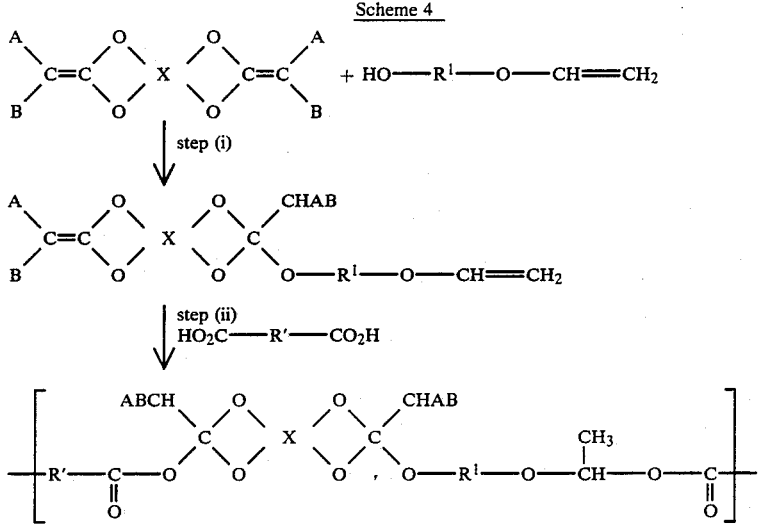

Scheme 5

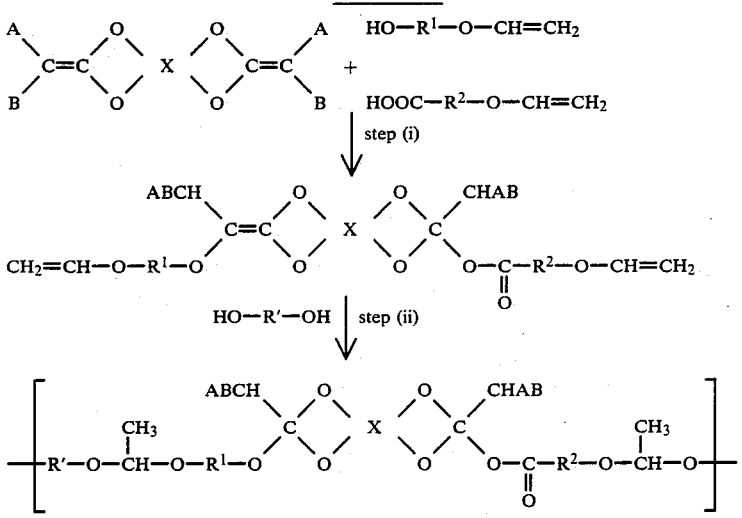

In Scheme 1, the selected diketene acetal is reacted with two equivalents of a monohydroxy vinyl ether in step (i), followed by the step (ii) reaction with a diol. As may be seen, the polymeric product contains mer units having acetal and ortho ester linkages.

In Scheme 2, the selected diketene acetal is reacted with two equivalents of a monocarboxy vinyl ether in step (i), followed by the step (ii) reaction with a diol. In this case, the polymeric product contains mer units having acetal, ortho ester and carboxy-ortho ester linkages.

In Scheme 3, the selected diketene acetal is reacted with one equivalent of a monohydroxy vinyl ether in step (i), followed by the step (ii) reaction with a diol. In this particular case, the polymeric product contains mer units having acetal and ortho ester linkages.

In Scheme 4, the selected diketene acetal is reacted with one equivalent of a monohydroxy vinyl ether in step (i), followed by the step (ii) reaction with a dicarboxylic acid. In this case, the polymeric product contains mer units having acetal, carboxy-acetal, ortho ester and carboxy-ortho ester linkages.

In Scheme 5, the selected diketene acetal is reacted with two equivalents of a mixture of a monohydroxy vinyl ether and a monocarboxy vinyl ether in step (i), followed by the step (ii) reaction with a diol. In this case, the polymeric product contains mer units having acetal, carboxy-ortho ester and ortho ester linkages.

In the examples illustrated in Schemes 1 through 5, the polymers formed in step (ii) are linear polymers because bifunctional reagents were used. It is clear, however, that if reagents having functionalities greater than two are used, crosslinked polymer structures will result. In these structures, all mer units are interconnected by covalent linkages.

Because acetals, carboxy-acetals, ortho esters and carboxy-ortho ester linkages all have different degrees of hydrolytic lability, controlling the relative amounts of these linkages in the linear or crosslinked polymers will control rate of bioerosion. In addition variations in the nature of the R groups will control the flexibility and other mechanical properties of the polymers.

The following examples further illustrate the polymers of the invention and the processes by which they may be prepared. These examples are not intended to limit the invention in any manner.

EXAMPLE 1

Under anhydrous conditions, 3.38 g (0.0159 mole) of 3,9-bis(ethylidene 2,4,8,10-tetraoxaspiro[5,5]undecane) (DETOSU) and 2.71 (0.0159 mole) of the monovinyl ether of trans-cyclohexane dimethanol were weighed into a 100 ml round bottom flask. The mixture was dissolved in 10 ml of distilled tetrahydrofuran and while stirring by means of a magnetic stirring bar, one drop of a p-toluenesulfonic acid solution in tetrahydrofuran (40 mg/ml) was added. Strict anhydrous conditions were maintained during stirring and catalyst addition. The addition reaction was exothermic and the solution temperature rapidly rose to about 45 °C. before gradually returning to room temperature. After stirring at room temperature for about 20 minutes, 0.22 g (0.0015 mole) of p-hydroxybenzoic acid was added and the reaction mixture was stirred for about one hour. Next, 2.06 g (0.01431 mole) of trans-cyclohexane dimethanol was added, followed by 0.1 ml of p-toluene sulfonic acid solution in tetrahydrofuran (40 mg/ml). The final reaction mixture was heated at 65° C. for 1 hr.

The polymer was isolated by precipitation into a large excess of methanol which contained a small amount of triethylamide as stabilizer, filtration of the precipitate and drying in a vacuum oven.

The polymer shown below was obtained.

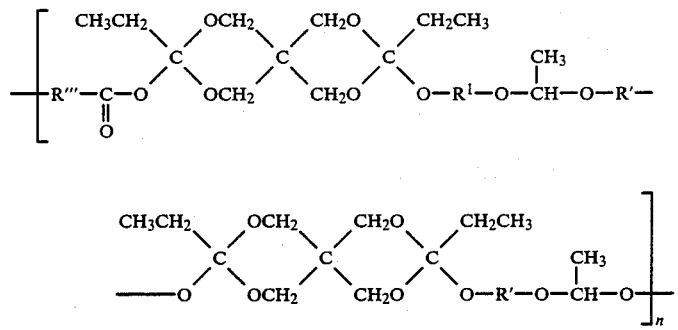

In this particular case, $R^1$, $R'$ and $R'''$ have the following structures:

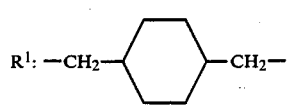

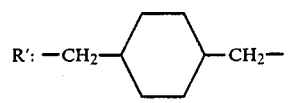

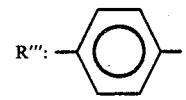

The infrared spectrum is shown in FIG. 1. The weight average molecular weight determined by gel permeation chromatography using polystyrene standards was 55,000 D.

EXAMPLES 2-5

Because the amount of the hydroxy-carboxylic acid monomer used in the polymerization process determines the hydrolytic lability of the polymer, a series of polymers containing varying amounts of the hydroxycarboxylic monomer were prepared.

Thus, following a procedure identical to that described under Example 1, 3.38 g (0.0159 mole) of DETOSU were reacted with 2.71 g (0.0159 mole) of the monovinyl ether of trans-cyclohexane dimethanol and the reaction product reacted with 0.414 g (0.0030 mole) of p-hydroxybenzoic acid and 1.86 g (0.0129 mole) of transcyclohexane dimethanol.

In a similar manner 3.38 g (0.0159 mole) of DETOSU were reacted with 2.71 g (0.0159 mole) of the monovinyl ether of trans-cyclohexane dimethanol and the reaction product reacted with 0.138 g (0.0010 mole) of p-hydroxybenzoic acid and 2.149 g (0.0149 mole) of transcyclohexane dimethanol.

In a similar manner 3.38 g (0.0159 mole) of DETOSU were reacted with 2.71 g (0.0159 mole) of the monovinyl ether of trans-cyclohexane dimethanol and the reaction product reacted with 0.041 g (0.0003 mole) of p-hydroxybenzoic acid and 2.250 g (0.0156 mole) of transcyclohexane dimethanol.

In a similar manner 3.38 g (0.0159 mole of DETOSU were reacted with 2.71 g (0.0159 mole) of the monovinyl ether of trans-cyclohexane dimethanol and the reaction product reacted with 2.293 g (0.0159 mole) of transcyclohexane dimethanol.

EXAMPLE 6

In certain instances it is advantageous to react one mole of DETOSU with two moles of the hydroxy-vinyl ether, to obtain the following reaction product:

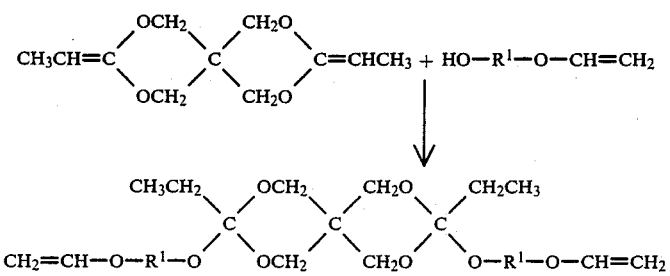

This intermediate can then be reacted with a diol to produce the following polymer:

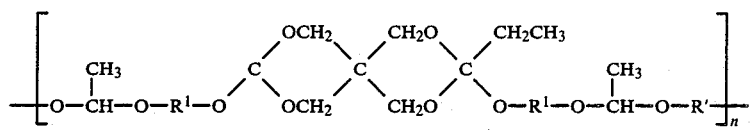

Procedure:
Under anhydrous conditions, 3.38 g (0.0159 mole) of DETOSU and 5.42 g (0.0318 mole) of the monovinyl ether of transcyclohexane dimethanol were weighed into a 100 ml round bottom flask. The mixture was dissolved in 10 ml of distilled tetrahydrofuran and while stirring by means of a magnetic stirring bar, one drop of a p-toluenesulfonic acid solution in tetrahydrofuran (40 mg/ml) was added. Strict anhydrous conditions were maintained during stirring and catalyst addition. The addition reaction was exothermic and the solution temperature rapidly rose to about 55° C. before gradually returning to room temperature. After stirring at room temperature for about 20 minutes, 2.29 g (0.0159 mole) of trans-cyclohexane dimethanol was added, followed by 0.1 ml of p-toluenesulfonic acid solution in tetrahydrofuran (40 mg/ml). The final reaction mixture was heated at 65° C. for 1 hr.

The polymer was isolated by precipitation into a large excess of methanol which contained a small amount of triethyl amine as stabilizer, filtration of precipitate and drying in a vacuum oven.

In this particular case $R^1$ and $R'$ had the following structure:

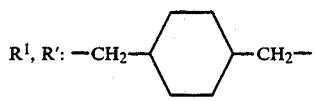

EXAMPLE 7

In certain instances it is advantageous to use a carboxy-vinyl ether compound to react with a diketene acetal. In such a case the following reaction product is obtained:

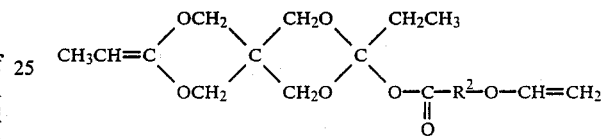

Thus, using a procedure identical to that described under Example 1, DETOSU is reacted with p-vinyloxymethyl cyclohexane carboxylic acid and the reaction product reacted with 1,4-butanediol. A polymer having the following structure is obtained:

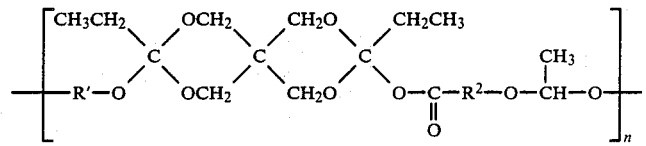

In this particular case $R^2$ and $R'$ have the following structures:

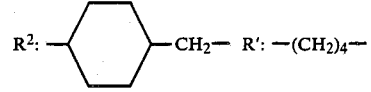

EXAMPLE 8

In certain instances it is advantageous to decrease the concentration of the highly reaction carboxy ortho ester linkages in the polymer by using a mixture of the reaction product between DETOSU and a hydroxy vinyl ether and the reaction product between DETOSU and a carboxy vinyl ether, that is the two compounds shown below:

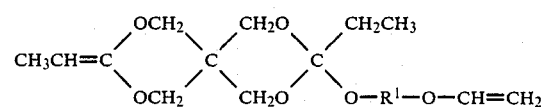

-continued

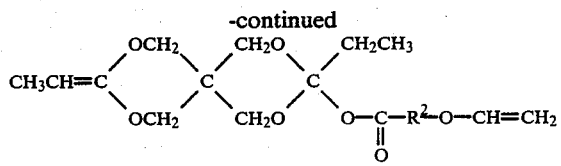

By allowing various ratios of these two compounds to react with a stoichiometric amount of diol, polymers having different degrees of hydrolytic lability can be obtained.

EXAMPLE 9

In certain instances it is advantageous to prepare a crosslinked polymer by using polyols having a functionality greater than two, e.g., as follows.

Under anhydrous conditions 2.12 g (0.01 mole) of DETOSU and 1.70 g (0.01 mole) of the monovinyl ether of trans-cyclohexane dimethanol were weighed into a small polyethylene bag. The mixture was thoroughly mixed by kneading the bag. Reaction started immediately without need of an acidic catalyst, the temperature rose to about 40° C. and then returned to room temperature within about one hour. Then 1.90 g (0.022 mole of OH groups) of LG 650 (a triol with R, as shown below, manufactured by Union Carbide Corporation) were weighed into the bag and 10 μl of a trichloroacetic acid solution in tetrahydrofuran (1 g/ml) were added. The viscous reaction mixture was again mixed well and then transferred from the polyethylene bag to an extruder and extruded into a Teflon tube having an internal diameter of about 3 mm. The Teflon tube was sealed at both ends and placed in a water bath at about 40° C. for about one day. After cure, the Teflon tube was slit lengthwise and the flexible product removed. Residual acidic catalyst was neutralized by placing the product in a flask and pressurizing the flask with ammonia. The crosslinked polymer had the following structure, where the lines indicate connection to polymer chains having similar structures to those shown:

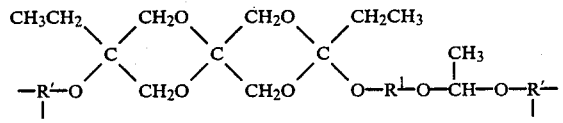

In this particular case R and R, had the following structures:

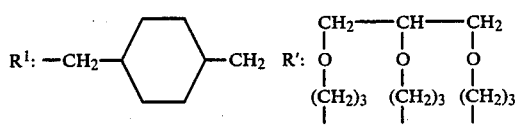

It should be noted that the crosslinked polymers prepared in this and the following examples may be characterized by FTIR or by the products obtained upon polymer hydrolysis. Typically, however, the linear polymers which serve as the precursors to the crosslinked structures are characterized by IR or other spectroscopic means, and the crosslinked structure is presumed therefrom.

EXAMPLE 10

Following the procedure described in Example 1 but replacing the monovinyl ether of trans-cyclohexane dimethanol with 1.16 g (0.01 mole) of the monovinyl ether of 1,4-butanediol, a crosslinked polymer was obtained where $R^2$ and $R'$ had the following structure:

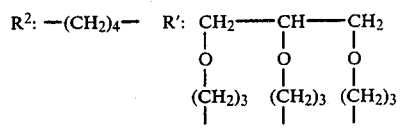

EXAMPLE 11

Following the procedure described in Example 1 but replacing LG 650 with 1.16 g (0.026 moles of OH groups) of 1,2,6-hexanetriol, a crosslinked polymer was obtained where $R^1$ and $R'$ had the following structures:

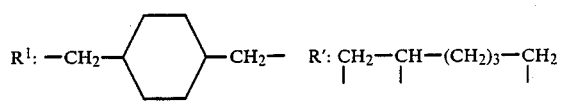

EXAMPLE 12

Following the procedure described in Example 11 but replacing LG 650 with 1.84 g (0.026 moles of OH groups) of propyl gallate, a crosslinked polymer was obtained where $R^1$ and $R'$ had the following structures;

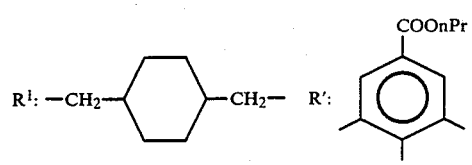

EXAMPLE 13

Following the procedure described in Example 1 but replacing LG 650 with 0.98 g (0.022 moles of OH groups) of 2-ethyl-2-(hydroxy methyl)-1,3-propanediol, a crosslinked polymer was obtained where $R^1$ and $R'$ had the following structures:

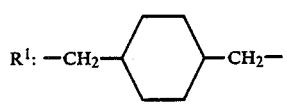

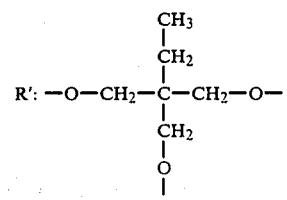

EXAMPLE 14

Following procedures similar to those already described, polymers based on ketene acetals other than DETOSU can be used. Examples of such diketene acetal monomers are shown in Table 1.

Modification of the above-described modes for carrying out the invention that are obvious to those of skill in the fields of polymer chemistry and sustained release dispensers are intended to be within the scope of the following claims.

We claim:

1. A linear or crosslinked biodegradable polymer containing a combination of the following mer units:

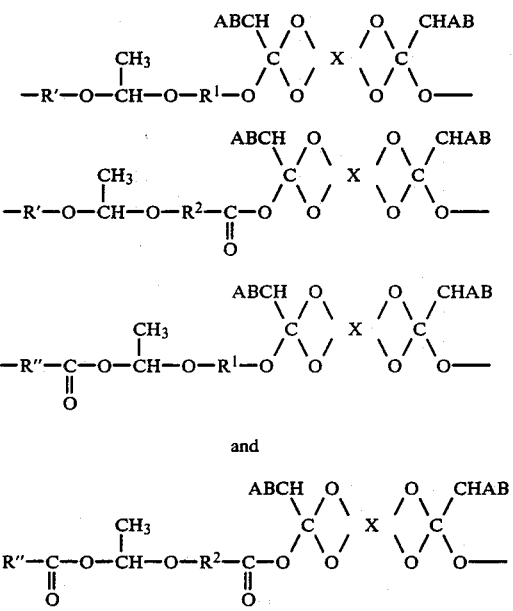

and wherein X is a quadrivalent organic grouping, A and B may be the same or different and are selected from the group consisting of hydrogen, and lower alkyl, and $R^1$, $R^2$, $R'$, $R''$ and $R'''$ may be the same or different and are selected from the group consisting of hydrocarbyl of 1 to 14 carbon atoms, oxyhydrocarbyl of 1 to 14 carbon atoms containing 1 to 4 oxy groups, and aryl of 1 to 4 rings, and wherein said $R^1$, $R^2$, $R'$, $R''$ and $R'''$ are unsubstitent or substituted with one or more longer alkyl, amino, nitro or halogen moieties.

2. The polymer of claim 1, wherein X is

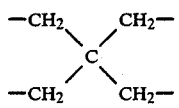

3. The polymer of claim 1, wherein X is a cyclohexyl moiety.

4. The polymer of claim 1, wherein A is hydrocarbyl and is saturated branched or straight-chain aliphatic or saturated cycloaliphatic.

5. The polymer of claim 1, wherein B is hydrocarbyl and is saturated branched or straight-chain aliphatic or saturated cycloaliphatic.

6. The polymer of claim 1, wherein $R'''$ is phenyl.

7. The polymer of claim 1, wherein the number of mer units in the polymer is in the range of 2 to 1000.

8. The polymer of claim 1, wherein the number of mer units in the polymer is in the range of 5 to 200.

9. A method for preparing a linear or crosslinked biodegradable polymer, comprising, under anhydrous conditions:

(i) reacting a diketene acetal having the formula

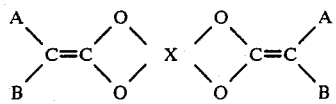

with at least one vinyl ether selected from the group consisting of mono-hydroxy vinyl ethers $HO-R^1-O-CH=CH_2$ and mono-carboxy vinyl ethers $HOOC-R^2-O-CH=CH_2$ to give an intermediate compound comprising a vinyl-terminated monomer; and (b) reacting said vinyl-terminated monomer with at least one compound given by $R'(OH)_n$, $R''(COOH)_n$, or $R'''(OH)_l(COOH)_m$, wherein n is an integer greater than or equal to 2, and l and m are integers greater than or equal to 1.

10. The method of claim 9, wherein the reactions of both step (i) and step (ii) are carried out in an aprotic solvent.

11. The method of claim 9, wherein the reaction of step (i) is carried out catalytically.

12. The method of claim 9, wherein the reaction of step (ii) is carried out catalytically.

13. A biodegradable beneficial agent dispenser comprising a body comprised of a dispersion of a beneficial agent in the polymer of claim 1.

14. A biodegradable beneficial agent dispenser comprising a body of a beneficial agent composition coated with the polymer of claim 1.

15. A biodegradable polymer containing the mer unit

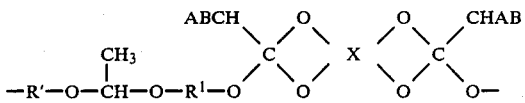

wherein X is a quadrivalent organic grouping, A and B may be the same or different and are selected from the group consisting of hydrogen and lower alkyl, and $R^1$ and $R'$ may be the same or different and are selected from the group consisting of hydrocarbyl of 1 to 1-4 carbon atoms, oxyhydrocarbyl of 1 to 14 carbon atoms containing 1 to 4 oxy groups, and aryl of 1 to 4 rings, and wherein said $R^1$ and $R'$ are unsubstituted or substituted with one or more lower alkyl, amino, nitro or halogen moieties.

16. A biodegradable polymer containing the mer unit

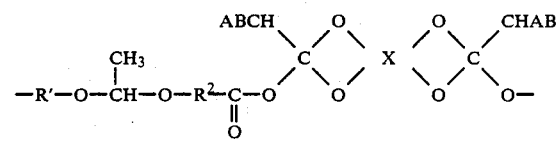

wherein X is a quadrivalent organic grouping, A and B may be the same or different and are selected from the group consisting of hydrogen and lower alkyl, and $R^2$ and $R'$ may be the same or different and are selected from the group consisting of hydrocarbyl of 1 to 14 carbon atoms, oxyhydrocarbyl of 1 to 14 carbon atoms containing 1 to 4 oxy groups, and aryl of 1 to 4 rings, and wherein said $R^2$ and $R'$ are unsubstituted or substituted with one or more lower alkyl, amino, nitro or halogen moieties.

17. A biodegradable polymer containing the mer unit

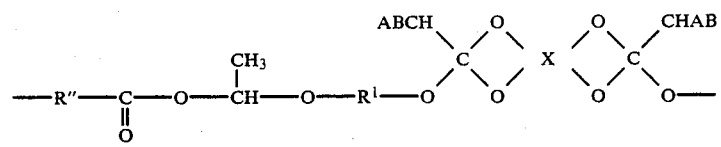

wherein X is a quadrivalent organic grouping, A and B may be the same or different and are selected from the group, consisting of hydrogen and lower alkyl, and $R^1$ and $R''$ may be the same or different and are selected from the group consisting of hydrocarbyl of 1 to 14 carbon atoms, oxyhydrocarbyl of 1 to 14 carbon atoms containing 1 to 4 oxy groups, and aryl of 1 to 4 rings, and wherein said $R^1$ and $R''$ are unsubstituted or substituted with one or more lower alkyl, amino, nitro or halogen moieties.

18. A biodegradable polymer containing the mer unit

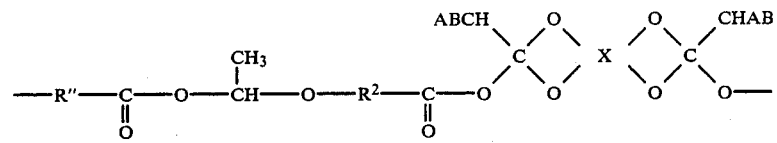

wherein X is a quadrivalent organic grouping, A and B may be the same or different and are selected from the group consisting of hydrogen and lower alkyl, and $R^2$ and $R''$ may be the same or different and are selected from the group consisting of hydrocarbyl of 1 to 14 carbon atoms, oxyhydrocarbyl of 1 to 14 carbon atoms containing 1 to 4 oxy groups, and aryl of 1 to 4 rings, and wherein said $R^2$ and p are unsubstituted or substituted with one or more lower alkyl, amino, nitro or halogen moieties.

19. The method of claim 9, wherein in step (a), said vinyl ether is $HO-R^1-O-CH=CH_2$, and in step (b), said at least one compound is $R'(OH)_n$.

20. The method of claim 9, wherein in step (a), said vinyl ether is $HO-R^1-O-CH=CH_2$, and in step (b), said at least one compound is $R''(COOH)_n$.

21. The method of claims 19 or 20, wherein n is 2 and the polymer is linear.

22. The method of claims 19 or 20, wherein n is 3 and the polymer is crosslinked.

23. The method of claim 9, wherein in step (a), said vinyl ether is $HO-R^1-O-CH=CH_2$, and in step (b), said at least one compound is $R'''(OH)_1(COOH)_m$.

24. The method of claim 23, wherein l and m are both equal to 1 and the polymer is linear.

25. The method of claim 23, wherein one of l and m is equal to 1 and the other is equal to 2, and wherein the polymer is crosslinked.

26. The method of claim 9, wherein in step (a), said vinyl ether is $HOOC-R^2-O-CH=CH_2$, and in step (b), said at least one compound is $R'(OH)_n$.

27. The method of claim 9, wherein in step (a), said vinyl ether is $HOOC-R^2-O-CH=CH_2$, and in step (b), said at least one compound is $R''(COOH)_n$.

28. The method of claims 26 or 27, wherein n is equal to 2 and the polymer is linear.

29. The method of claims 26 or 27, wherein n is equal to 3 and the polymer is crosslinked.

30. The method of claim 9, wherein in step (a), said vinyl ether is $HOOC-R^2-O-CH=CH_2$, and in step (b), said at least one compound is $R'''(OH)_1(COOH)_m$.

31. The method of claim 30, wherein l and m are both equal to 1.

32. The method of claim 30, wherein one of l and m is equal to 1 and the other is equal to 2.

33. The method of claim 9, wherein in step (a), said at least one vinyl ether comprises both a mono-hydroxy vinyl ether $HO-R^1-O-CH=CH_2$ and a mono-carboxy vinyl ether $HOOC-R^2-O-CH=CH_2$, and in step (b) said at least one compound is $R'(OH)_n$.

34. The method of claim 33, wherein in step (a), said at least one vinyl ether comprises both a mono-hydroxy vinyl ether $HO-R^1-O-CH=CH_2$ and a mono-carboxy vinyl ether $HOOC-R^2-O-CH=CH_2$, and in step (b) said at least one compound is $R'(COOH)_n$.

35. The method of claims 33 or 34 wherein n is equal to 2 and the polymer is linear.

36. The method of claims 33 or 34 wherein n is equal to 3 and the polymer is crosslinked.

37. The method of claim 9, wherein in step (a), said at least one vinyl ether comprises both a mono-hydroxy vinyl ether $HO-R^1-O-CH=CH_2$ and a mono-carboxy vinyl ether $HOOC-R^2-O-CH=CH_2$, and in step (b) said at least one compound is $R'''(OH)_1(COOH)_m$.

38. The method of claim 37, wherein l and m are both equal to 1 and the polymer is linear.

39. The method of claim 37, wherein one of l and m is equal to 1 and the other is equal to 2, and wherein the polymer is crosslinked.

* * * * *